United States Patent [19]

Vassiliades

[11] Patent Number: 5,009,919

[45] Date of Patent: Apr. 23, 1991

[54] FINGER-PRINTING SYSTEMS & METHOD

[76] Inventor: Anthony E. Vassiliades, 8738 Tanager Woods Dr., Cincinnati, Ohio 45249

[21] Appl. No.: 320,808

[22] Filed: Mar. 8, 1989

Related U.S. Application Data

[63] Continuation of Ser. No. 938,260, Dec. 5, 1986.

[51] Int. Cl.[5] .......... A61B 5/117

[52] U.S. Cl. .......... 427/1; 118/31.5

[58] Field of Search .......... 118/31.5; 427/1, 150

[56] References Cited

U.S. PATENT DOCUMENTS 4,232,083 11/1980 Buerkley .......... 427/1

4,379,198 4/1983 Meadows et al. .......... 427/1

4,578,690 3/1986 Veillette et al. .......... 427/150

FOREIGN PATENT DOCUMENTS 0015392 2/1981 Japan .......... 427/1

*Primary Examiner*—Janyce Bell

*Attorney, Agent, or Firm*—Sigalos, Levine & Montgomery

[57] ABSTRACT

A fingerprinting system comprising means capable of releasably retaining a liquid and a liquid composition releasably retained in said means, said liquid composition comprising a leuco chromogenic compound and an oleophilic solvent therefor, and a substrate for receiving fingerprints associated therewith, said substrate being coated on at least a portion of one surface thereof with a color-developing substance capable of reacting with said chromogenic compound to produce a colored reaction product. The invention also comprises the method of fingerprinting utilizing such system.

10 Claims, No Drawings

FINGER-PRINTING SYSTEMS & METHOD

This application is a continuation of application Ser. No. 938,260, filed Dec. 5, 1986.

BACKGROUND OF THE INVENTION

The present invention relates to inkless fingerprinting systems used for identification purposes. More specifically, it relates to compositions, systems, and methods of generating instant, stable fingerprints on various substrates without the need of conventional inks and without the use of any chemical or mechanical post-treatment of the fingerprint or the surface on which the fingerprint was made.

As used herein the term "fingerprints" also encompasses "footprints" such as those taken of newly-born infants and placed on birth records. Also, the term "inkless" means the absence of colored pigments such as carbon black and as being distinct from printing inks as such term is now understood in this art.

The fingerprint patterns or ridge endings and ridge separations are highly individualized and are not altered with time. The comparison of fingerprint patterns has long been accepted as an absolute means of identifying individuals in a multitude of criminal and non-criminal situations.

In order for a fingerprinting identification system to be commercially acceptable it must be extremely stable and reliable, i.e., the prints must be distinct and clear and must be easily readable by the human eye and by automated fingerprint reading systems which are finding increased usage especially with a number of law enforcement agencies. Furthermore, the prints must form instantaneously, and must possess a high degree of stability toward exposure to extreme atmospheric conditions such as temperature, humidity and light. Preferably, the systems must be simple and aesthetically inoffensive.

Traditionally, fingerprints have been made with printing or writing types of ink, usually comprising finely ground carbon black particles dispersed in a liquid vehicle. The carbon black dispersion is ordinarily applied to a flat and firm surface, the excess dispersion removed, transferred to the surface of the object to be fingerprinted or identified, and subsequently transferred to the surface of the substrate where the final print is to be made. Such a procedure is cumbersome, time consuming and results in severe soiling of the hands and clothing of everyone involved in the fingerprinting process.

During the past several years inkless fingerprinting systems have been proposed such as disclosed in U.S. Pat. No. 3,831,552 involving the use of magnetizable powders. Other proposed inkless systems utilize the chelation of specific metal salts such as sodium vanadate with organic acids as described in U.S. Pat. No. 2,082,735, or various methods of reacting 8-hydroxyquinoline with metal salts, and preferably ferric chloride, as described in U.S. Pat. Nos. 3,960,632, 4,262,623, and 4,379,178. Additionally, U.S. Pat. No. 4,232,083 discloses the use of metal complexing compounds having a plurality of ligand groups with transitional metal salts of oleophilic, organic acids to form dark images which can be useful in fingerprinting systems.

The inkless fingerprinting systems known heretofore possess varying degrees of undesirable properties. Some are mechanically too complex to find commercial application and others, especially those relying upon metal-chelation reactions, are usually too slow and the image of the fingerprint does not appear instantaneously and in some cases it takes long periods of time before the print develops its full intensity. Oftentimes, these slow-forming inkless fingerprinting systems can be rendered completely inoperable if fingerprinting is attempted in substantially lower than ambient temperature as would be the case in an outdoor environment in geographic locations with extremely cold climates. In some cases, the fingerprint is treated chemically or mechanically after it is made in order to develop its desired color and color intensity.

SUMMARY OF THE INVENTION

It has now been discovered that highly reactive, aesthetically attractive, and extremely stable, black fingerprints can be provided which eliminate the problems of the prior art. The fingerprints produced by the present invention are clean and with a high degree of sharpness and image intensity and are produced rapidly and by a simple procedure. Additionally, the hue and intensity of these prints remain almost intact even after prolonged exposures to atmospheric conditions of light, temperature and humidity. Even though a wide variety of hues can be produced, the preferred color of the fingerprints of the present invention is black.

Briefly stated, the present invention comprises a fingerprinting system comprising means capable of releasably retaining a liquid and a liquid composition releasably retained in said means, said liquid composition comprising a leuco chromogenic compound and an oleophilic solvent therefor, and a substrate for receiving fingerprints associated therewith, said substrate being coated on at least a portion of one surface thereof with a color-developing substance capable of reacting with said chromogenic compound to produce a colored reaction product.

The invention also comprises the method of fingerprinting as hereinafter described.

DETAILED DESCRIPTION

The essential components of the instant fingerprinting compositions are the chromogenic compounds, color-developing substances, and the liquid vehicle.

The chromogenic compounds are leuco dye intermediates which possess the unique property of being colorless in neutral or alkaline media, but become colored when they react with an acidic or electron accepting substance. These dyes are, per se, well known and examples thereof which can be used in this invention are crystal violet lactone (CVL), dilactones, benzoyl leuco methylene blue (BLMB), derivatives of bis-(p-dialkylaminoaryl) methane, xanthenes, indolyls, auramines, fluorans and bisfluorans such as those described in U.S. Pat. Nos. 2,981,733, 2,981,738, 3,669,711, 3,681,390, 3819,396, 3,821,010 and 4,302,393.

There is a multitude of known electron-accepting color-developing substances capable of reacting with the leuco chromogenic compounds, which can be used in the present invention, and which have been described in the prior art. Among such electron-accepting substances are acidic clays such as montmorillonites, kaolins, bentonites and attapulgites, low molecular weight phenol-aldehyde condensation products (novolaks) and/or their metal salts as disclosed in U.S. Pat. Nos. 3,427,180, 3,672,935, and 3,723,156, and derivatives of aromatic carboxylic acids and/or their metal salts as disclosed in U.S. Pat. Nos. 3,488,207, 3,864,146, 3,871,900, 3,934,070, 3,983,292, 4,303,719, and 4,372,583. Specific examples of such color-developing materials usable in the present invention are: 3-phenyl salicylic acid, 3,5-di-tertiary butyl salicylic acid, octyl salicylic acid, 2-hydroxy-1-benzyl-3-naphthoic acid, 2-hydroxy-4-methyl-5-isobutyl thiobenzoic acid, 3,3'-thiobis (2-hydroxy-5-methyl) benzoic acid, 2-hydroxy-5-butyl sulfonyl benzoic acid, condensation products of salicylic acid and salicylic acid derivatives, United Catalyst's Copisil, a montmorillonite clay, low molecular weight condensation products of p-phenyl phenol with formaldehyde, p-cyclohexyl phenol-formaldehyde condensation product, and p-tertiary-amylphenol-formaldehyde condensation product.

These color developers may be formulated in several different ways by preparing water-based conventional coatings containing adhesives or binders such as natural or modified starches, latexes, hydrolyzed polyvinyl alcohols, proteins and the like, and (optionally) inorganic pigments such as inert clays, calcium carbonate, titanium dioxide and others, and applied onto the substrate to which the fingerprint is to be applied by conventional paper coaters such as air-knife, gate-roll, blade, reverse rolls and the like. The use of inorganic pigments is a preferred mode of this invention insofar as pigments, generally, have a high affinity for oleophilic materials like the ones used in the present invention to dissolve the leuco dyes and thus absorb quickly the oil-dye solution during transfer of the solution from the finger to the substrate.

Alternatively, these color-developing materials can be formulated into "fountain solutions" or "inks" using water-miscible solvents such as alcohols and ketones, or water-immiscible solvents such as xylenes, toluenes, benzenes and the like.

The "fountain solutions" and "inks" may be applied to the substrate on commercial printing presses using various printing methods such as wet and dry offset, flexographic, and direct letter and other conventional printing methods and equipment. The use of printing presses to apply color developers is of particular importance in this invention insofar as several security applications require the fingerprinting of only one or two digits. In general, it is simpler and less costly for both the manufacturer and the user of fingerprinting systems if only the relatively smaller area of a document where the fingerprints will be applied is spot-coated, or spot printed with the color-developing substance.

The solvents used in the present invention must possess good solvating characteristics for the dyes and the color-developing substances to enable and enhance the reaction between the two materials. Additionally, the solvents to be used in the fingerprinting systems of the instant invention must have low evaporation rates for prolonged shelf life in the pad, good flow properties for rapid and complete transfer from the pad to the finger and from the finger to the substrate, be clear in color to avoid interference with the final hue of the fingerprint, and exhibit no adverse toxicological effects. Exemplary of the solvents in this invention are alkylated phenols such as monoisobutyl biphenol and monoisopropyl biphenol, chlorinated paraffins, alkylated naphthalenes, partially hydrogenated terphenyls such as Monsanto'HB-40, soya-bean oil, cottonseed oil, coconut oil, ester alcohols such as Eastman Kodak's Texanol, alkylated glycol ethers and ether acetates such as Eastman Kodak's Ektasolve series, and combinations thereof.

Critical to the instant invention are the careful selection of the type and amount of the chromogenic compounds, nature of the various color-developing substances; particularly their pH, and the physical and chemical properties of the solvent. The type of chromogenic compound selected will determine the hue or color of the final print or image and the amount of the chromogenic compound must be properly balanced depending upon the type of the color-developing substance used to ensure the desired final intensity, speed, and stability of the final print or image. The solvent used with any particular combination of chromogenic compound(s) and color-developing substance(s) must possess good solvating or dispersing properties for the components to be dissolved and/or dispersed in the solvent, give good flow properties for easy and complete transfer of the composition from the pad to the finger and from the finger to the substrate, and have a low evaporation rate for prolonged shelf-life in the fingerprinting pad. Moreover, the acidity; or lack of it, of the solvent used can affect the exact hue of the final print or image depending upon the chromogenic compound used.

Additionally, single component leuco dyes which give a true black image are unknown to date. Nearly black images can be produced with fluoran type of leuco dyes such as described in U.S. Pat. No. 3,681,390. These nearly black prints obtained from the fluoran leuco dyes are of rather low intensity, and their hue and stability varies greatly depending upon the coreactant or the color developer chosen. Oftentimes, other leuco dyes have to be combined with the nearly black fluorans to produce truer black prints. The combination of various classes of leuco dyes, however, often results in undesirable fade characteristics of the images with aging, especially upon exposure to conditions of high temperature, humidity and light. By the proper and careful selection of leuco dyes in this invention, it is possible to produce intense, rapidforming and stable black fingerprints using a variety of color developers. This can be done by routine experimentation, with suitable combinations being set forth in the examples herein.

However, by operating within the parameters disclosed herein, one skilled in this art can by routine experimentation determine for any particular chromogenic compound or mixture thereof the most suitable color-developing substance and solvent and proportions thereof to give the desired final hue or color and a final print having the desired intensity and stability.

In accordance with this invention, fingerprints of almost any color can be produced; the preferred color, however, is black.

In one mode of this invention, the fingerprinting solution is prepared by dissolving the leuco dye in the solvent and then impregnating a fingerprinting pad with the solution. A fingerprinting system, usually comprising a container housing means capable of releasably retaining a fluid (such as any conventional felt or blotter material pad now conventionally used for fingerprinting) is suitable.

The color-developing substance is coated, as previously noted, onto the substrate. Such substrate can be any substance capable of retaining a fingerprint; most suitably paper. Conventional components, such as binders, viscosity modifiers, wetting and dispersing agents, defoamers and the like can be used with the color developer in their usual amounts for their usual effect. These are used presently, for example, with the color-developer in making transfer sheets for carbonless paper systems. The particular amounts for any given color developer can be determined by routine experimentation.

The only portion of the substrate that need be coated with the color-developing substance is that which is to receive the fingerprints.

In use, the finger or fingers are simply coated with the colorless liquid composition by pressing them onto the fingerprinting pad or otherwise applying the liquid composition to them, and then the finger(s) pressed onto the coated substrate. A color immediately develops only on the area(s) where the pressure of the finger(s) has been applied. There is no soiling of the fingers.

As to proportions, the color developer need only be coated onto the paper in an amount sufficient to give the acidity necessary to develop the proper color, as is conventionally done in making coated front (CF) papers in carbonless copying paper systems.

In another mode of the present invention, the inkless fingerprinting solution is prepared by sequentially dissolving the leuco dye(s) in the same solvent and adding small amounts of polyvalent metallic ions such as zinc, cadmium, nickel, aluminum, magnesium, and manganese in the form of salts; such as chlorides or octoates, to the solution prior to impregnating the pad. The addition of the metallic ions seems to catalyze the dye-color developer reaction and significantly increase the intensity and the rate of appearance of the final fingerprint. Furthermore, since the metallic ions themselves are electron-accepting species they can act as the sole color-developing substances in this invention. It is preferable, however, to use them in combination with one or more of the other color-developing substances described earlier.

It has also been found during the development of this invention that the addition of small amounts (between 0.5% and 2.0% of the weight of the inkless solution) of ultra violet absorbers such as nickel bis(octyl phenol) sulfide, hydroxy benzophenones, hydroxy benzotriazoles and the like, to the inkless fingerprinting solutions can further improve the stability of the fingerprints during prolonged exposures to light.

The invention will be further described in connection with the examples that follow, which are set forth for purposes of illustration only without intending to limit the scope of the invention.

The following leuco dyes with their respective designation in parentheses were used in the examples and obtained from Ciba-Geigy: Pergascript Black (I-BR), Pergascript Blue I-2R, crystal violet lactone (CVL), Pergascript Green (I-GD), Pergascript Red (I-6B), and Pergascript Orange (I-5R); Benzoyl Leuco Methylene Blue (BLMB) was obtained from Hilton Davis Chemical Company. Also used are soya-bean oil (SBO), Sybron's isopropyl biphenyl (IPBP), butyl biphenal (BB), and Monsanto's partially hydrogenated terphenyl (HB-40). Unless otherwise noted, all percentages and parts are by weight.

Extraneous components such as binders, viscosity modifiers, wetting and dispersing agents, defoamers and the like used in making the final coating or printing compositions have been omitted from most of the examples for the sake of brevity. Such components do not constitute a critical part of the present invention; they are significant only to the extent that they must be properly adjusted according to the coating or printing method to be used in order to facilitate the ease of application of the color developer onto the substrate, and to produce a functional coated or printed final product. Moreover, as noted above, the use of such components is well known to the paper-making, paper-coating, and printing industries.

The invention will be further described in connection with the following examples which are set forth for purposes of illustration only.

EXAMPLE 1

A standard fingerprinting pad was impregnated with an inkless solution; which solution was prepared by dissolving the following leuco dyes in 96 parts of HB-40: 3.1 parts of I-BR, 1.0 part of CVL, 3.3 parts of I-GD, 0.8 parts of I-6B and 0.3 parts of BLMB.

Separately, a color developer surface was prepared by coating a paper substrate with a dispersion containing 40 dry parts of United Catalyst's Copisil (a montmorilonite clay), 100 parts of water, 10 dry parts of Dow's latex 620, 2 dry parts of oxidized starch, and sufficient NaOH to raise the pH of the dispersion to 9; the coating weight of the dispersion was about 4 grams per square meter.

When the edge of a finger was placed on the fingerprinting pad, a clear colorless oil was transferred from the pad to the finger and when the same finger was placed on the paper surface coated with the color developer a deep black, clear fingerprint was formed instantaneously.

COMPARATIVE EXAMPLE 1a

This example illustrates the invention wherein a change in the solvent affects the color of the inkless fingerprint.

Example 1 was repeated, but 96 parts of monoisopropyl biphenol was used as the solvent of the inkless fingerprinting solution instead of the HB-40. The fingerprints produced were of deep greenish color.

COMPARATIVE EXAMPLE 1b

This example, along with comparative example 1c below, illustrates the invention wherein a change in the color-developer substance without the proper adjustment in the leuco dye(s) solution will alter the final results significantly.

Example 1 was repeated, but the color-developing substance used was a condensation product of p-phenyl phenol with formaldehyde. The fingerprints obtained were of blue-greenish color and of lower color intensity.

COMPARATIVE EXAMPLE 1c

Comparative Example lb was repeated, but the inkless fingerprinting solution was prepared by dissolving in 96 parts of HB-40 the following leuco dyes: 4 parts of I-BR, 1 part of I-GD, 0.2 parts of I-6B and 1.0 part of BLMB. Clear, black fingerprints of high color intensity were obtained.

EXAMPLE 2

Example 1 was repeated, but the color developer substance was Huber's Hydrasperse clay (kaolin) instead of Copisil. Equivalent results were obtained.

EXAMPLE 3

Example 1 was repeated, but the color developer substance used was the condensation product of octyl salicylic acid with formaldehyde instead of the Copisil, and the pH of the coating dispersion was raised to 11 with ammonium hydroxide. Equivalent results were obtained.

COMPARATIVE EXAMPLE 3a

This example illustrates the effect of the pH of the color developer on the hue of the final fingerprint.

Example 3 was repeated, but the pH of the color developer coating was adjusted to about 8 using an aqueous solution of zinc chloride. The color of the final fingerprint was dark green.

EXAMPLE 4

Example 1 was repeated, but the inkless fingerprinting solution was made by dissolving in 50 parts of HB-40 the following leuco dyes: 2 parts of I-BR, 0.2 parts of I-GD, 0.2 parts of I-6B, and 0.5 parts of BLMB. Clear, black fingerprints were obtained.

EXAMPLE 5

Example 3 was repeated, but the color-developer substance used was 3,5,di-tertiary butyl salicylate. Equivalent results were obtained.

EXAMPLE 6

A fingerprinting pad was impregnated with an inkless solution prepared by dissolving 1.6 parts of I-BR, 0.2 parts of I-GD, 0.2 parts of I-6B and 0.25 parts of BLMB in 50 parts of monoisobutyl biphenyl.

Fingerprints were made on a paper substrate containing 2-hydroxy-4-methyl-5-isobutyl thiobenzoic acid as the color-developing material. Black, highly distinct, intense fingerprints were obtained.

EXAMPLE 7

Example 1 was repeated, but 10 gms of a 16% solution of zinc octoate in mineral spirits were mixed with the inkless fingerprinting solution prior to impregnating the pad. Fingerprints of even higher intensity than those in Example 1 were obtained.

EXAMPLE 8

Example 6 was repeated, but the inkless fingerprinting solution was prepared by dissolving 2.2 parts of I-BR, 1.1 parts of I-6B, 2.3 parts of I-GD and 0.6 parts of CVL in 94 parts of monoisopropyl biphenyl. Equivalent results were obtained.

EXAMPLE 9

Example 6 was repeated, but the color developing substance was 5-octyl salicylic acid. Equivalent results were obtained.

EXAMPLE 10

Example 9 was repeated, but the color-developing substance was the zincated salt of 5-octyl salicylic acid. Fingerprints of even higher intensity than those in Example 9 were obtained.

EXAMPLE 11

A pad was impregnated with an inkless solution which was prepared by dissolving 3.2 parts of I-BR, 0.2 parts of CVL, 0.5 parts of I-GD and 0.6 parts of BLMB in 50 parts of monoisopropyl biphenyl and 45 parts of HB-40.

Fingerprints made on a paper substrate containing the condensation product of p-tertiary-amylphenol with formaldehyde as the color developer were distinct and of intense black color.

EXAMPLE 12

A paper surface was printed flexographically with a printing solution containing the oligomeric condensation products of 5-octyl salicylic acid with formaldehyde as the color-developing substances. Fingerprints were made on the printed surface from a pad impregnated with an inkless solution which solution was prepared by dissolving 3.2 parts of I-BR, 0.1 part of CVL, 0.25 parts of I-GD and 0.30 parts of BLMB in 81 parts of HB-40 and 11 parts of monoisobutyl biphenol. The fingerprints were black and of high intensity.

EXAMPLE 13

Example 11 was repeated, but 15 parts of a 16% solution of zinc octoate were mixed with the inkless fingerprinting solution. Equivalent results were obtained.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A fingerprinting system comprising means capable of releasably retaining a liquid and a liquid composition releasably retained in said means, said liquid composition consisting essentially of a leuco chromogenic compound and an oleophilic solvent therefor, a substrate for receiving fingerprints associated therewith, said substrate being coated on at least a portion of one surface thereof with a color-developing substance capable of reacting with said chromogenic compound to produce a colored reaction product; and polyvalent metallic ions in said liquid composition or on said substrate with said color-developing substance.

2. The system of claim 1 wherein said means is a fingerprint pad and said substrate is paper.

3. The system of claim 1 or 2 wherein said leuco chromogenic compound is a combination of leuco dyes capable of giving a true black print.

4. A fingerprinting system comprising means capable of releasably retaining a liquid and a liquid composition releasably retained in said means, said liquid composition consisting essentially of a leuco chromogenic compound, an oleophilic solvent therefore, and polyvalent metallic ions, and substrate for receiving fingerprints associated therewith, said substrate being coated on at least a portion of one surface thereof with a color-developing substance capable of reacting with said chromogenic compound to produce a colored reaction product.

5. The system of claim 1 or 2, wherein said color-developing substance is selected from acidic clays, low molecular weight phenol-aldehyde condensation products or their metal salts, derivatives of aromatic carboxylic acids or their metal salts, or mixtures thereof.

6. The method of fingerprinting comprising applying to a member to be fingerprinted a liquid composition consisting essentially of a leuco chromogenic compound and an oleophilic solvent therefor and applying the member to be fingerprinted to a substrate coated at least in the portion thereof to which the member is applied with a color-developing substance capable of reacting with said leuco chromogenic compound to produce a colored reaction product which is a print of the member; and polyvalent metallic ions in said liquid composition or on said substrate with said color-developing substance.

7. The method of claim 6 wherein the leuco chromogenic compound is a combination of leuco dyes capable of giving a true black print.

8. The method of fingerprinting comprising applying to a member to be fingerprinted a liquid composition consisting essentially of a leuco chromogenic compound, an oleophilic solvent therefor, and polyvalent metallic ions, and applying the member to be fingerprinted to a substrate coated at least in the portion thereof to which the member is applied with a color-developing substance capable of reacting the said leuco chromogenic compound to product a colored reaction product which is a print of the member.

9. The system of claim 4 wherein said means is a fingerprint pad and said substrate is paper.

10. The method of claim 8 wherein the leuco chromogenic compound is a combination of leuco dyes capable of giving a true black print.

* * * * *